(12) United States Patent
Christiansen (10) Patent No.: US 12,012,593 B2
(45) Date of Patent: Jun. 18, 2024

(54) MODIFIED PEPTIDE DISPLAY

(71) Applicant: Miti Biosystems GmbH, Vienna (AT)

(72) Inventor: Guntram Christiansen, Mondsee (AT)

(73) Assignee: Miti Biosystems GmbH, Vienna (AT)

( * ) Notice: Subject to any disclaimer, the term of this patent is extended or adjusted under 35 U.S.C. 154(b) by 0 days.

(21) Appl. No.: 17/727,975

(22) Filed: Apr. 25, 2022

(65) Prior Publication Data

US 2022/0325274 A1 Oct. 13, 2022

Related U.S. Application Data

(60) Division of application No. 16/361,099, filed on Mar. 21, 2019, now Pat. No. 11,332,734, which is a continuation of application No. 15/011,245, filed on Jan. 29, 2016, now abandoned, which is a division of application No. 13/814,487, filed as application No. PCT/EP2011/063138 on Jul. 29, 2011, now Pat. No. 9,249,411.

(30) Foreign Application Priority Data

Aug. 13, 2010 (EP) .................................. 10172788

(51) Int. Cl.
- *C40B 40/02* (2006.01)
- *C07K 1/04* (2006.01)
- *C12N 15/10* (2006.01)
- *C40B 40/10* (2006.01)
- *C40B 50/06* (2006.01)

(52) U.S. Cl.
CPC .......... *C12N 15/1037* (2013.01); *C07K 1/047* (2013.01); *C12N 15/1082* (2013.01); *C40B 40/02* (2013.01); *C40B 40/10* (2013.01); *C40B 50/06* (2013.01)

(58) Field of Classification Search
None
See application file for complete search history.

(56) References Cited

U.S. PATENT DOCUMENTS

| | | |
|---|---|---|
| 2007/0207502 A1 | 9/2007 | Benkovic |
| 2009/0137424 A1 | 5/2009 | Tsao |
| 2009/0143295 A1 | 6/2009 | O'Brien |

FOREIGN PATENT DOCUMENTS

| | | |
|---|---|---|
| EP | 1187914 B1 | 5/2005 |
| EP | 2048155 A1 | 4/2009 |
| EP | 2141175 A1 | 1/2010 |
| JP | 2009112286 A | 5/2009 |
| WO | 95014714 A1 | 6/1995 |

(Continued)

OTHER PUBLICATIONS

Kuipers (Aug. 9, 2010) Microbial production of thioester-stabilized peptides, PhD Thesis, University of Groningen, pp. 1 to 125.*

(Continued)

*Primary Examiner* — Christian C Boesen
(74) *Attorney, Agent, or Firm* — Prismatic Law Group, PLLC; Ronald J. Kamis (57) ABSTRACT

The invention refers to a replicable genetic package displaying a peptide having at least one intramolecular cyclic bond between two heteroatoms of amino acid side chains, a method of preparing a replicable genetic package, a method of producing a library and a library of replicable genetic package.

10 Claims, 3 Drawing Sheets
Specification includes a Sequence Listing.

KRVRSPLEKQADKPIQLKAPFGAFFLEIFNVKKLLFAIPLVEPFYSHSMSKNVKVSAPK AVPFFARFLAEQAVEANNSNSAPYGNTMKYPSDWEEYSAETVESCLAKSHTENSFI NVWKDDKTLDRYANYEGCLWNATGVVVCTGDATQCYGTWVPIGLAIPENEGGGSE GGGSEGGGSEGGGTKHPDYGDTPIPGYTYINPLDGTYPPGTEQNLANLILLLRSLSLL ILSCFRIICSTNRQGA

(56) References Cited

FOREIGN PATENT DOCUMENTS

| WO | 2000023465 | A1 | 4/2000 |
|---|---|---|---|
| WO | 0077194 | A1 | 12/2000 |
| WO | 2002101026 | A2 | 12/2002 |
| WO | 2006062398 | A2 | 6/2006 |
| WO | 2007047301 | A1 | 11/2007 |
| WO | 2009098450 | A1 | 8/2009 |
| WO | 2011018227 | A1 | 2/2011 |
| WO | 2012005578 | A1 | 1/2012 |
| WO | 2016/102434 | A1 | 6/2016 |
| WO | 2016102434 | A1 | 6/2016 |

OTHER PUBLICATIONS

Buczek et al., Cell. Mal. Life Sci. 62 (2005) 3067-3079.
Duquesne et al., Nat Prod Rep. Aug. 2007;24(4):708-34.
Giebel et al., Biochemistry, vol. 34, Jan. 1, 1995, pp. 15430-15435.
Hallen et al., Proc Natl Acad Sci USA. Nov. 27, 2007 104{48}: 19097-101.
Koivunen et al., Bio/Technology vol. 13, No. 3, Mar. 1, 1995, pp. 265-270.
Kasal et al., 2009 Eur. J_ Phycol. 44:49-62.
Ladner, Trends in Biotechnology 13:10 Oct. 1, 1995, pp. 426-430.
Maqueda et al., FEMS Microbial Rev. Jan. 2008; 32(1):2-22.
Matthews et al., Science, vol. 260, May 21, 1993, pp. 1113-1117.
Millward et al., ACS Chemical Biology, Sep. 21, 2007, vol. 2, No. 9, pp. 625-634.
Mitchell et al, J Biol Chem. May 8, 2009; 284(19):13004-12.
Morris et al., J Am Chem Soc. Apr. 29, 2009; 131(16): 5946-55.
Oman et al., Nature Chemical Biology 6:9-18, 2010.
Philmus et al., Chembiochem, 2008, 9(18), 3066-3073.
Saska et al., J Biol Chem. Oct. 5, 2007;282(40):29721-8.
Schmidt et al., Proc Natl Acad Sci USA May 17, 2005;102(20):7315-20.
Walton et al., Biopolymers May 26, 2010. Epub ahead of print 2010;94(5):659-64 doi: 10.1002/bip.21416.
Willey et al., Annu. Rev. Microbial. 2007 61:477-501.
Yin et al., Chemistry and Biology, Current Biology, London, vol. 14, No. 3, Mar. 23, 2007, pp. 303-312.
Ziemert et al., Angew Chem Int Ed Engl. 2008;47(40):7756-9.
International Search Report: PCT/EP2011/063138; Oct. 17, 2011: pp. 1-8.
Written Opinion of International Search Authority: PCT/EP2011/063138; Oct. 17, 2011: pp. 1-8.
International Preliminary Report On Patentability: PCT/EP2011/063138; Feb. 19, 2013: pp. 1-9.
Extended European Search Report: EP10172788.1 Jan. 24, 2011: pp. 1-7.
Sancheti et al., Advanced Drug Delivery Reviews, (2009) vol. 61, No. 11, pp. 908-917, Elsevier, Amsterdam, NL.
Jung, Letters in Peptide Science, 2001, 8:(3-5):259-265.
Kang et al., Science, 2007, vol. 318, No. 5856, pp. 1625-1628.
Forsgren et al., Journal of Molecular Biology, Apr. 2, 2010, vol. 397, No. 3, pp. 740-751.
Azzazy et al., 2002, Clinical Biochemistry Review 35, pp. 425-445.
Kuipers, Anneke, "Microbial production of thioether-stabilized peptides", PhD Thesis, University of Groningen, Published Aug. 9, 2010; 125 pages.
Tjalsma et al., 2000, Microbiology and Molecular Biology Reviews 64, 515-547.
Urban et al., Nature Communications, Nov. 15, 2017 8:1500, 1-10; DOI: 10.1038/s41467-017-01413-7.

\* cited by examiner

AAACGGGTTAGATCTCCCCTCGAAAAGCAAGCTGATAAACCGATACAATTA
AAGGCTCCTTTTGGAGCCTTTTTTTGGAGATTTTCAACGTGAAAAAATTATTATTC
GCAATTCCTTTAGTGGAACCTTTCTATTCTCACTCGATGTCCAAAAATGTTAAAGTC
TCTGCGCCCAAAGCAGTCCCCTTCTTTGCTCGTTTCTTAGCAGAGCAAGCCGTGG
AAGCTAACAATTCTAATTCTGCTCCTTACGGTAATACTATGAAGTATCCTTCCGATT
GGGAAGAATATTCGGCCGAAACTGTTGAAGTTGTTTAGCAAATCCCATACAGA
AAATTCATTTATTAACGTCTGGAAGACGACAAAACTTTAGATCGTTACGCTAACTA
TGAGGGCTGTCTGTGGAATGCTACAGGCGTTGTAGTTTGTACTGGTGACGCAACT
CAGTGTTACGGTACATGGGTTCCTATTGGGCTTGCTATCCCTGAAAATGAGGGTG
GTGGCTCTGAGGGTGGCGGTTCTGAGGGTGGAGGTTCTGAGGGTGGCGGTACT
AAACATCCTGACTACGGTGATACACCTATCCCGGGCTATACTTTATCAACCCTCTC
GACGGCACGTATCCTCCTGGTACTGAGCAAAACCTCGCTAATCTAATCCTTCTCTT
GAGGAGTCTCAGCCTCTTAATACTTTCATGTTTCAGAATAATATGTTCCACAAATA
GGCAGGGGGCTTAAACTGTTTATACGGTATCCTGTTTACTCCAA

Fig. 1b

KRVRSPLEKQADKPIQLKAPFGAFFLEIFNVKKLLFAIPLVEPFYSHSMSKNVKVSAPK
AVPFFARFLAEQAVEANNSNSAPY<u>GNTMKYPSDWEEY</u>SAETVESCLAKSHTENSFI
NVWKDDKTLDRYANYEGCLWNATGVVVCTGDATQCYGTWVPIGLAIPENEGGGSE
GGGSEGGGSEGGGTKHPDYGDTPIPGYTYINPLDGTYPPGTEQNLANLILLLRSLSLL
ILSCFRIICSTNRQGA

MODIFIED PEPTIDE DISPLAY

CROSS-REFERENCE TO RELATED APPLICATIONS

This application is a divisional of U.S. application Ser. No. 16/361,099 filed on Mar. 21, 2019, which is a continuation of U.S. application Ser. No. 15/011,245 filed on Jan. 29, 2016, which is a divisional of U.S. application Ser. No. 13/814,487 filed on Apr. 1, 2013 which is a 371 National Phase of International Patent Application WO PCT/EP2011/063138 filed on Jul. 29, 2011, which claims priority to European patent application 10172788.1 filed on Aug. 13, 2010, the content of each of which applications is incorporated herein by reference.

INCORPORATION OF SEQUENCE LISTING

This application contains a sequence listing submitted electronically via EFS-web, which serves as both the paper copy and the computer readable form (CRF) and consists of a file entitled "WRMTB1DIV_seqlist.txt", which was created on Apr. 25, 2022, which is 4,676 bytes in size, and which is herein incorporated by reference in its entirety.

The invention refers to a display system, to present peptides which are post-translationally modified.

BACKGROUND

The search for new compounds in many cases makes use of large libraries of compounds to screen and identify a compound that has a desired activity or characteristic. Combinatorial peptide library technology is a valuable resource for drug discovery and development. Recombinant peptide libraries displayed on phage or other viral particles have proven especially useful in such screens. Numerous groups are working to develop biologically active peptides obtained from peptide libraries in the search of novel treatments for many human diseases and illnesses.

Phage-displayed peptide library technology has been widely used in the search of novel treatments for many human diseases and illnesses. Peptide libraries displayed on filamentous phage have been used as a screening resource for identifying peptides bound to any given target thereby showing pharmacologic effects. Peptides so identified can subsequently be synthesized in bulk using conventional synthetic chemistry methods.

The bacteriophage M13 is a non-enveloped filamentous *Escherichia coli* phage of the Inoviridae family with a single stranded (ss)DNA genome. The nucleocapsid consists of four bacteriophage proteins with different copy numbers: pVIII approximately 2700 copies while pIII, pVI and pIX are present in 5 copies. Among other, bacteriophages like T4, T7, fd and lambda, M13 has been successfully used for phage display for use in a biotechnological screening method. In such a screening approach a random library of peptides is presented on the surface of the nucleocapsid of the phage M13 to study interaction of the different phages with a binding partner (protein-protein, protein-DNA, etc). Usually synthetic oligonucleotides are cloned into genes coding for proteins which constitute the nucleocapsid and thereby the peptide of interest (or a library of different peptides) is presented on the surface of the phage M13 nucleocapsid for subsequent binding studies.

The phage display methods typically involve the insertion of random oligonucleotides into a phage genome such that they direct a bacterial host to express peptide libraries fused to phage coat proteins (e. g., filamentous phage pIII, pVI or pVIII). The advantages of this technique are in the small dimension of the phage allowing to handle libraries with up to $10^{15}$ different individuals and in the physical linkage of the displayed peptides with the genetic information that encode them.

The basic phage display technology has been expanded to include peptide libraries that are displayed from replicable genetic packages other than phage, such as eukaryotic viruses, bacteria and yeast cells. The principles and strategy are closely analogous to those employed for phage, namely, that nucleic acids encoding peptides to be displayed are inserted into the genome of the package to create a fusion protein between the peptides to be screened and an endogenous protein that is exposed on the cell or viral surface. Expression of the fusion protein and transport to the cell surface results in display of peptides at the cell or viral surface.

In an effort to increase diversity of a library though a secondary peptide structure some groups have produced conformationally-constrained peptides through chemical reactions.

EP1187914B1 discloses a library of structurally-constrained peptides comprising a plurality of cyclic peptides stabilized through disulfide bridges between cystein residues.

WO2009/098450A2 discloses a phage particle displaying a disulfide-stabilized bicyclic peptide linked via a connector compound.

US2009/0137424A1 discloses the posttranslational modification of phage displayed polypeptides, which contain unnatural amino acids to provide targets for azide-alkyne [3+2]cycloaddition reactions and Staudinger modifications.

The biosynthesis of depsipeptide natural compounds is described in EP2048155A1. A precursor peptide sequence of between 5 and 50 amino acids is modified by an ATP-grasp-like enzyme. The nucleic acid molecule is introduced e.g. into *E. coli* to produce the depsipeptide natural compounds, for example microviridin.

Natural product synthesis of several ribosomal peptides is reviewed by Oman et al (Nature Chemical Biology 6:9-18 (2010)). Precursor peptides are post-translationally processed mediated by leader peptides. These leader peptides assist in folding the precursor peptide, stabilizing the precursor against degradation and keeping the precursor inactive during the biosynthesis inside the host until the appropriate time for secretion and proteolysis.

There is a pressing need for new targeting peptides developed through peptide library technology. It is, thus, the objective of the present invention to provide an improved library of structurely constrained peptides for screening purposes.

SUMMARY OF THE INVENTION

The solution to this technical problem is achieved by providing the embodiments characterised in the claims. Accordingly, the present invention allows to easily create large libraries of polycyclic peptides through enzymatically processing by post-translationally modifying (PTM) enzymes.

According to the invention there is provided a replicable genetic package displaying a peptide having at least one intramolecular cyclic bond between two heteroatoms of amino acid side chains, including intramolecular isopeptide bonds, ester bonds or lanthionine bonds.

The replicable genetic package according to the invention preferably is selected from the group consisting of a phage particle, a bacterium, a yeast, a fungus, a spore of a microorganism and a ribosome.

Specifically the replicable genetic package is selected from the group consisting of M13, T4, T7, fd and lambda phages.

According to a specific aspect said peptide is a precursor peptide comprising a leader and a core peptide.

It is preferred that said leader peptide comprises a leader of a natural ribosomal peptide.

It is also preferred that said core peptide is derived from a natural ribosomal peptide.

Specifically the cyclic bond is linking two atoms selected from the group consisting of C, N, O and S.

In a preferred embodiment the cyclic bond is linking two different atoms selected from the group consisting of C, N, O and S.

According to a preferred embodiment the peptide comprises a polycyclic structure.

It is preferred that the peptide comprises a randomised sequence.

According to another aspect of the invention there is provided a method of preparing a replicable genetic package displaying a peptide having at least one intramolecular cyclic bond within amino acid side chains, such as a replicable genetic package according to the invention, comprising
  a) providing a nucleic acid sequence encoding a peptide,
  b) ligating said nucleic acid sequence into the gene of a replicable genetic package,
  c) displaying the corresponding primary peptide sequence on the surface of said replicable genetic package to obtain a primary package, and
  d) enzymatically processing said primary package with a post-translationally modifying (PTM) enzyme to produce a mature package displaying a cyclic structure of said peptide.

In a specific embodiment the method provides for an intramolecular cyclic bond between two heteroatoms of amino acid side chains.

The preferred method according to the invention further comprises engineering a peptide to block the peptide cleavage.

The preferred PTM enzyme is selected from the group consisting of carboxylate-amine ligases, cyclases, dehydrogenases, decarboxylases, epimerases, hydroxylases, peptidases, dehydratases, transferases, esterases, oxygenases and isomerases, in particular lanthionine bond forming enzymes, cytolysin forming enzymes, cyanobactin forming enzymes, thiopeptide forming enzymes, conopeptide forming enzymes, microviridin forming enzymes, cyclotide forming enzymes, bacteriocin forming enzymes and subtilosin forming enzymes.

According to a specific embodiment the processing is performed in the presence of a leader, preferably a leader peptide.

According to the invention there is further provided a replicable genetic package obtainable or obtained by the method according to the invention.

According to a further aspect of the invention there is provided a method of producing a library of replicable genetic packages displaying a peptide having at least one intramolecular cyclic bond within amino acid side chains, such as replicable genetic package according to the invention, comprising
  a) providing a repertoire of nucleic acid sequences encoding peptide variants,
  b) ligating said repertoire into the genes of replicable genetic packages,
  c) displaying the corresponding primary peptide sequences on the surface of said packages to obtain a primary library, and
  d) enzymatically processing said primary library with a PTM enzyme to produce a mature library displaying cyclic structures of said peptide variants.

According to a further aspect of the invention there is provided a library of replicable genetic packages, produced according to the method of the invention, including the method of preparing the replicable genetic package and the method of producing a library of replicable genetic packages.

According to a further aspect of the invention there is provided a library of replicable genetic packages, such as those according to the invention, wherein the packages display a variety of peptide sequences.

Yet, according to another aspect of the invention there is provided a method of post-translationally modifying a peptide library with a PTM enzyme to produce a mature library displaying polycyclic peptide structures.

Specifically an enzyme is used, which is capable of providing a covalent bond between two atoms selected from the group consisting of C, N, O and S, either the same or different atoms.

Thus, according to the invention there is further provided the use of a PTM enzyme to process a peptide library to incorporate polycyclic structures into peptide variants.

FIGURES

FIG. 1: Sequences. Sequence of the pIII gene fused to mvdE, (FIG. 1a, SEQ ID No. 2); Translated amino acid sequence (FIG. 1b, SEQ ID No. 3): phage protein pIII, bold letters refer to the MvdE precursor peptide, underlined letters refer to the core peptide.

DETAILED DESCRIPTION OF THE INVENTION

Therefore the present invention relates to a peptide display system based on replicable genetic packages which display peptides having a specific intramolecular cyclic structure. Metabolic engineering of peptides is advantageous over chemical crosslinking, e.g. to engineer disulfide bridges, since it employs heteroatoms as bridge piers of the heterocycles. Thereby a variety of peptide primary and secondary structures is provided through metabolic processing as a pool for specifically selecting suitable peptides bearing highly desirable binding motifs.

The term "replicable genetic package" as used herein shall mean a prokaryotic or eukaryotic genetic package, and includes cells, spores, yeasts, bacteria, viruses, bacteriophages, ribosomes and polysomes. A preferred replicable genetic package is a phage. The peptides are displayed on the replicable genetic package, i.e. they are attached to a group or molecule located at an outer surface of the replicable genetic package. The replicable genetic package is a screenable unit comprising a peptide to be screened linked to a nucleic acid molecule encoding the peptide. The nucleic acid molecule usually is replicable either in vivo, e.g. as a vector, or in vitro, e.g. by PCR, transcription and translation. In vivo replication can be autonomous such as for a cell, with the assistance of host factors, such as for a virus, or with the assistance of both host and helper virus, such as for a phagemid. Replicable genetic packages displaying a variety of peptides are formed by introducing nucleic acid molecules encoding heterologous peptides to be displayed into the genomes of the replicable genetic packages to form fusion proteins with autologous proteins that are normally expressed at the outer surface of the replicable genetic packages. Expression of the fusion proteins, transport to the outer surface and assembly results in display of the peptides from the outer surface of the replicable genetic packages. The display system as used according to the invention usually refers to a collection of peptides that are accessible for selection based upon a desired characteristic, such as a physical, chemical or functional characteristic, whereupon a nucleic acid encoding the selected peptide can be readily isolated or recovered. The display system preferably provides for a suitable repertoire of peptides in a biological system, sometimes called a biological display system, which specifically refers to replicable genetic packages. Contrary to in vitro display systems, the biological systems typically employ a viral or cellular expression system, e.g. expressing a library of nucleic acids in transformed, infected, transfected or transduced cells and display of the encoded peptides on the surface of the replicable genetic package.

The term "peptide" as used herein shall mean a peptide or polypeptide that contains 5 or more amino acids, typically at least 10, preferably at least 20, more preferred at least 30, more preferred at least 40, more preferred at least 50, more preferred at least 60, 70, 80, 90 or 100 amino acids. The term also refers to higher molecular weight polypeptides, such as proteins.

The term "intramolecular cyclic bond" as used herein shall mean a secondary structure formed through intramolecular isopeptide bonds, which employ covalent bonding between side chains of amino acids within a peptide sequence, e.g. without incorporating extramolecular (exogenous) structures. The term shall specifically refer to those cycles and polycycles that have been obtained through post-translational enzymatic processing, which would preferably exclude chemical processing, such as disulfide bridge formation, e.g. through reduction reaction, cycloaddition or Staudinger reactions. Specifically the cycle is a heterocycle including at least two atoms herein called "heteroatoms", which are either heteroatoms, such as N, O or S, or atoms forming a covalent bond between two different atoms selected from the group consisting of C, N, O and S. This specifically includes C—N, C—O, C—S, N—N, N—O, N—S, O—O, O—S and S—S bonding, in an appropriate chemical sense including double bonds. Any of the bridge piers of such bonding are referred to as "heteroatoms", and considered as bridge piers of "heterocycles", specifically those heterocycles produced by post-translational modification or metabolic processing The term "polycycle" or "polycyclic structure" as used herein shall refer to at least a bicyclic structure, preferably a structure having at least three, more preferred at least four, even more preferred at least five cyclic bonds. Depending on the length of the peptide as used according to the invention a more complex secondary peptide structure can be achieved.

The term "precursor peptide" as used herein shall refer to a peptide including elements supporting the post-translational enzymatic processing (maturation) of the peptide, e.g. a signal and/or leader sequence operationally linked to a core peptide. The carboxyl terminus of the precursor peptide usually encodes the sequence that is enzyme-modified, the "core sequence". Though the leader is usually cleaved from the mature carboxyl terminus following modification, resulting in a short peptide product, the preferred precursor peptide displayed according to the invention would still include the precursor element, such as the signal or leader sequence, even after maturation of the core peptide. Thus, the preferred display system or construct is engineered to block the cleavage of the core peptide either before and/or after the maturation process. This may be effected by a mutation to prevent cleavage or through establishing suitable bridges crossing the cleavage site.

The term "leader" or "leader sequence" as used herein shall refer to a recognition motif for a post-translationally modifying (PTM) enzyme. According to a preferred aspect the peptide is displayed either with an integrated leader sequence on the replicable genetic package, e.g. in the form of a precursor peptide, or the leader may be provided as a separate entity, e.g. as a separate peptide independent of the replicable genetic package according to the invention, such as an additive or by means of a helper display system, which is based on biological or in vitro display systems displaying a leader sequence or a variety of leader sequence mutants to act in support of the PTM enzymatic action.

The term "natural ribosomal peptide" also called "ribosomal peptide natural products" as used according to the invention shall mean biologically active, ribosomally synthesized peptides of structural diversity, most commonly around 100 amino acids long, which are post-translationally modified by various enzymes that catalyze the formation of a large number of different chemical motifs. Within this class, there are numerous (precursor) peptides with hypervariable sequences. The primary peptides can act as substrates for the processing pathways, and so each pathway leads to numerous different mature peptides. Members of this class have a high potential possibly important in microbiology, the environment, medicine and technology. Commonly, the precursor peptide of a natural ribosomal peptide contains a relatively conserved leader sequence that is at least partly responsible for recognition by the modifying enzymes and/or by export machinery. These biosynthetic mechanisms are nearly universal for the bacterial ribosomal peptide natural products and are also commonly found in the biosynthesis of similar peptides from other organisms, such as archea, fungi, plants and animals.

The preferred ribosomal peptides as used according to the invention include microviridins, lacticins, thiopeptides, conopeptides, microcins, cytolysins, lantibiotics, cyanobactins, amatoxins/phallotoxins, cyclotides and (cyclic) bacteriocins, or functionally equivalent variants thereof.

The term "randomisation" or "randomised sequence" shall refer to specific nucleotide or amino acid sequence modifications in a predetermined region, e.g. forming new bridge piers of heterocycles upon metabolic processing, or between such bridge piers changing the three-dimensional structure of the heterocycle. Modification typically results in random insertion, exchange or deletion of amino acids. For substituting or inserting amino acids a selection of amino acids or the whole range of natural or synthetic amino acids may be used randomly or semi-randomly by methods known in the art and as disclosed in the present patent application. Randomisation will result in a repertoire of nucleic acids encoding a variety of peptide sequences. The use of natural amino acids is preferred for randomisation purposes. In specific embodiments the use of unnatural amino acids is avoided.

The term "repertoire" as used herein refers to a collection of nucleic acid or amino acid sequences that are characterized by sequence diversity. The individual members of a repertoire may have common features, such as a common core structure within a scaffold, and/or a common function, e.g. a specific binding or biological activity. Within a repertoire there are usually "variants" of a nucleic acid or amino acid sequence, such as a variety of peptide sequences, which are derived from a parent sequence through mutagenesis methods, e.g. through randomisation techniques. The term "library" as used herein refers to a mixture of heterogeneous peptide or nucleic acid sequences. The library is composed of members, each of which has a single peptide or nucleic acid sequence. To this extent, "library" is synonymous with "repertoire." Sequence differences between library members are responsible for the diversity present in the library.

The term "functionally equivalent variant" or "functionally active variant" of a parent molecule as used herein means a sequence resulting from modification of this sequence by insertion, deletion or substitution of one or more amino acids or nucleotides within the sequence or at either or both of the distal ends of the sequence, and which modification does not affect (in particular impair) the activity of this sequence. In the case of a ligand binding peptide having specificity to a selected ligand, the functionally active peptide variant as used according to the invention would still have the predetermined binding specificity, though this could be changed, e.g. to change the fine specificity to a specific epitope, the affinity, the avidity, the Kon or Koff rate, etc. In a preferred embodiment the functionally active variant a) is a biologically active fragment of the peptide, the functionally active fragment comprising at least 50% of the sequence of the peptide, preferably at least 70%, more preferably at least 80%, still more preferably at least 90%, even more preferably at least 95% and most preferably at least 97%, 98% or 99%; b) is derived from the peptide by at least one amino acid substitution, addition and/or deletion, wherein the functionally active variant has a sequence identity to the peptide of at least 50%, preferably at least 60%, more preferably at least 70%, more preferably at least 80%, still more preferably at least 90%, even more preferably at least 95% and most preferably at least 97%, 98% or 99%. The functionally active variant may be obtained by sequence alterations in the peptide or the nucleotide sequence, wherein the sequence alterations retains a function of the unaltered peptide or the nucleotide sequence, when used in combination of the invention. Such sequence alterations can include, but are not limited to, (conservative) substitutions, additions, deletions, mutations and insertions.

The variant of the polypeptide or the nucleotide sequence is functionally active in the context of the present invention, if the activity of the peptide preparation including the variant (but not the original) amounts to at least 10%, preferably at least 25%, more preferably at least 50%, even more preferably at least 70%, still more preferably at least 80%, especially at least 90%, particularly at least 95%, most preferably at least 99% of the biological activity of the peptide as used according to the invention including the peptide or the nucleotide sequence without sequence alteration (i.e. the original polypeptide or the nucleotide sequence).

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

In another embodiment of the invention the peptide or the nucleotide sequence as defined above may be modified by a variety of chemical techniques to produce derivatives having essentially the same activity (as defined above for fragments and variants) as the peptide, and optionally having other desirable properties.

As used herein, a "homologue" or "functional homologue" shall mean that variants of a parent nucleic acid, peptide, polypeptide or proteins have the same or conserved residues at a corresponding position in their primary, secondary or tertiary structure. The term also extends to two or more nucleotide sequences encoding homologous peptides. In particular, homologous compounds usually have at least about 50% amino acid sequence identity with regard to a full-length native sequence or any fragment thereof. Preferably, a homologous compound will have at least about 55% amino acid sequence identity, more preferably at least about 60% amino acid sequence identity, more preferably at least about 65% amino acid sequence identity, more preferably at least about 70% amino acid sequence identity, more preferably at least about 75% amino acid sequence identity, more preferably at least about 80% amino acid sequence identity, more preferably at least about 85% amino acid sequence identity, more preferably at least about 90% amino acid sequence identity, more preferably at least about 95% amino acid sequence identity to a native compound, or any other specifically defined fragment of a full-length compound. When the function as a biologically active peptide is proven with such a homologue, the homologue is called "functional homologue".

The term "homologous nucleotide sequences" as used herein refers to nucleotide sequences which are related but not identical in their nucleotide sequence with the contemplated nucleotide sequence, and perform essentially the same function. These are also meant to encompass variations in its nucleotide composition including variations due to the degeneracy of the genetic code, whereby the nucleotide sequence performs essentially the same function.

"Percent (%) amino acid sequence identity" with respect to the peptide sequences identified herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

The term "post-translationally modifying enzyme" or "PTM enzyme" as used herein shall refer to enzymes involving structural changes of a translated peptide, e.g. specifically modifying natural ribosomal peptides in the biosynthesis of biologically active peptides as part of the processing machinery. This class includes multiple types of enzymes, including carboxylate-amine ligases, cyclases, dehydrogenases, cyclodehydratase decarboxylases, epimerases, hydroxylases, peptidases, dehydratases, transferases, esterases, oxygenases and isomerases, specifically lanthionine bond forming enzymes, cytolysin forming enzymes, cyanobactin forming enzymes, thiopeptide forming enzymes, conopeptide forming enzymes, microviridin forming enzymes, cyclotide forming enzymes, bacteriocin forming enzymes and subtilosin forming enzymes.

Further description of the enzymes is provided below.

Specifically lanthionine bond forming enzymes are employed. Lantibiotics (Willey and van der Donk Annu. Rev. Microbiol. 2007. 61:477-501) are defined as lanthionine-containing antibiotics. Intramolecular bridges are termed lanthionine or methyllanthionine bonds, which are arising from the posttranslational modification of different amino acid side chains. Serine and threonine hydroxyl groups are dehydrated to yield 2,3-didehydroalanine (Dha) or (Z)-2,3-didehydrobutyrine (Dhb), respectively. This is followed by the stereospecific intramolecular addition of a cysteine residue onto Dha or Dhb to form the lanthionine or methyllantionine bond. Currently several posttranslationally modifying enzymes and their genes are known: LanB type dehydratases are shown to constitute the C-terminus of the enzyme proposed to catalyse the dehydration step of serine and threonine. LanC type cyclases catalyses the addition of cysteine thiols. LanC, the cyclase component, is a zinc metalloprotein, whose bound metal has been proposed to activate the thiol substrate for nucleophilic addition. LanM type fused dehydratases and cyclases: It is responsible for both the dehydration and the cyclization of the precursor-peptide during lantibiotic synthesis. LanD oxidative decarboxylase type enzymes: This enzyme catalyses the removal of two reducing equivalents from the cysteine residue of the C-terminal meso-lanthionine of epidermin to form a —C═C— double bond. LanP type peptidases are cleaving the leader peptide from the lantibiotics. LanT type peptidase fused to an ABC transporter;

the cleavage of precursor peptide is mediated by the transporter as part of the secretion process. LtnM and LtnJ type of dehydratase and dehydrogenase involed in the formation of D-alanine. CinX hydroxylates asparagines during cinnamycin biosynthesis.

Microcins: (Duquesne et al [Nat Prod Rep. 2007 August; 24(4):708-34] are mostly produced by enterobacteria and classified in three groups: Class I, IIa and IIb. Involved PTM enzymes and their genes are: McbB like serine and cysteine dehydratases (cyclodehyratases), McbC like flavine dependent dehydrogenase (oxidoreductase), TldE protease involved in proteolytic processing of the antibiotic Microcin B17, PmbA (TldD) microcin processing peptidase 2 type, MccB type modification enzyme involved in Microcin MccC7/C51 biosynthesis, MccD type transfer of n-aminopropanol groups (MccC7/C51), McjB and McjC involved in Microcin J25 processing and maturation, MceC type glycosyltransferase involved in Microcin E492 modification, MceD enterobactin esterase, Mcel acetyltransferase.

The further group of cytolysin forming enzymes is preferably employed. Streptolysins (Mitchell et al, J Biol Chem. 2009 May 8; 284(19):13004-12) are posttranslationally modified peptides from *Clostridium botulinum*. Specific PTM enzymes are: SagB a dehydrogenase and SagC a serine and cysteine dehydratases (cyclodehydratase). Both enzymes are involved in the formation of thiazole and (metyl)-oxazole formation.

Cyanobactins (Schmidt et al Proc Natl Acad Sci USA. 2005 May 17; 102(20):7315-20) are cyclic peptides containing heterocycles isolated from different cyanobacterial genera. According to a preferred embodiment cyanobactin forming enzymes may be used such as PatA a subtuilisin like serine protease peptidase which cleaves the precursor peptide, PatD a serine and cysteine dehydratases (cyclodehyratases) and PatG a dehydrogenase (oxidoreductase).

Thiopeptides (Morris et al J Am Chem Soc. 2009 Apr. 29; 131(16): 5946-552009) are a class of heterocycle-containing posttranslationally modified peptides which have a characteristic tri- and tetrasubstituted pyridine ring at the junction of the macrocycle. Involved PTM enzymes are TpdB dehydratase involved in the pyridine ring formation, TpdC dehydratase involved in the pyridine ring formation, TpdG cysteine dehydratase (cycloydehyratase) involved in thiazoline formation, TpdE dehydrogenase (oxidoreductase) thiazoline to thiazole formation, TpdH peptidase, TpdI radical SAM protein, coproporphyrinogen III oxidase, TpdJ1 P450 monooxygenase, TpdJ2 P450 monooxygenase, TpdL radical SAM protein involved in the C-methylation, TpdM O-methyltransferase, TpdN deamine reductase, TpdO cyclodehydratase, TpdP dehydratase, TpdQ P450 Monooxygenase, TpdT N-methyltransferase and TpdU radical SAM protein.

Conopeptide forming enzymes are also preferred. Conopeptides (Buczek et al Cell. Mol. Life Sci. 62 (2005) 3067-3079) are a class of postranslationally modified peptides produced by cone snails. It is estimated that the class of conopeptides constitute a group of 100.000 different peptides. Specific PTM enzymes are Tex31 a substrate-specific endoprotease, MrPDI a specific protein disulfide isomerase, a vitamin K-dependent carboxylase (Accno: AF382823). From biochemical experiments it could be shown that the following enzyme reactions are involved in conotoxin formation: a proline, valine, lysine hydroxylation, a protein amidating reaction by a specific monooxygenase, the tryptophan bromination to 6-bromotryptophan by a specific bromo peroxidase, and epimerization of Trp, Leu, Phe, Val by an epimerase. Further there are a glutaminyl cyclase, a tyrosyl sulfo transferase, and an O-glycosyltransferase involved in conotoxin biosynthesis.

Amatoxins/Phallotoxins (Walton et al Biopolymers. 2010 May 26. [Epub ahead of print], Hallen et al Proc Natl Acad Sci USA. 2007 Nov. 27; 104(48):19097-101) are posttranslationally modified peptides isolated from *Amanita* basidiomycetes. A specifically known PTM enzyme is Pop1 a serine protease. From biochemical experiments it is deduced that a cyclase, a hydroxylase, and an enzyme involved in tryptophan-cysteine tryptathione cross linking is involved in the formation of amatoxin/phallotoxin production.

Microviridin forming enzymes are specifically preferred. Microviridins (Philmus et al., 2008 see above, Ziemert et al., Angew Chem Int Ed Engl. 2008; 47(40):7756-9): Microviridins are a class of tricyclic peptides, which have been isolated from different cyanobacterial genera. The PTM enzymes involved in the maturation of the Microviridins have been biochemically characterized. Specific PTM enzymes are MvdB an acetyltransferase, MvdC a cyclization protein involved in the amide bond formation, similar to RimK ATP-binding proteins, ATP grasp ligase, MvdD cyclization protein involved in the formation of the two ester bonds, similar to RimK ATP-binding proteins and ATP grasp ligases.

Cyclotides (Saska et al J Biol Chem. 2007 Oct. 5; 282 (40):29721-8) are a group of posttransaltionally modified peptides isolated from plants of the Violaceae, Rubiaceae and Curcurbitaceae families. Among the characterized PTM enzymes are two peptidases involved in cyclotide formation: NbVpe1a and NbVpe1b.

Circular bacteriocins (Maqueda et al FEMS Microbiol Rev. 2008 January; 32(1):2-22) belong to a group of post-translationally modified peptides isolated from Gram-positive bacteria. Although the gene operons which are coding for the enzymes responsible for the formation of circular (cyclic) bacteriocins have been isolated and described, the identification of biochemical steps catalyzed by the candidate enzymes has not been completed. From biochemical experiments it has been deduced that a peptidase, which catalyzes a hed-to tail circularization is involved in circular bacteriocin formation. The epimerization of an L-alanine to a D-alanine is catalyzed by a specific epimerase. Also preferred are subtilosin forming enzymes, like AlbA a Fe—S Oxidoreductase, AlbF a Zn-dependent peptidase and AlbE a second Zn-dependent peptidase.

Also preferred are subtilosin forming enzymes, like AlbA AP011541.1Fe—S Oxidoreductase, AlbF AP011541.1Zn-dependent peptidase and AlbE AP011541.1Zn-dependent peptidase.

Among the preferred PTM enzymes there are proteases that cleave the peptide product from the leader peptide. Usually the PTM enzyme modifies a precursor peptide that contains a leader sequence that is at least partly responsible for recognition by the modifying enzymes and/or by export machinery. However, the leader may as well be provided as a separate entity, such as an additive or by co-expression employing a co-expression vector that contains the leader sequence. The peptide and the leader may then be co-expressed in the same recombinant host and the peptide is post-translationally modified. Alternatively, the leader and the enzyme may be provided as an additive to the recombinant host cell culture, which host is then capable of expressing the mature peptide. The PTM enzyme typically modifies cysteine, serine and threonine residues, but also carboxyl groups of asparagine or glutamine, e.g. to form heterocyclic moieties, such as thiazole and oxazole moieties by post-translational processing. Therefore the PTM enzyme may act as a single protein or a single-subunit enzyme, as well as a protein enzyme complex comprising at least two, three or four different enzymes to support the heterocyclization. Specifically genes or gene clusters involved in the biosynthesis of heterocyclic ribosomal peptides, including functionally active variants or homologues, may be employed in accordance with the present invention. Natural enzymes may be preferably used, e.g. of natural origin such as from lysates of organisms. Specifically enzymes of bacterial origin are preferably used, such as derived from a bacterial lysate. Alternatively, recombinant enzymes may be used. According to another preferred embodiment, improved enzymes or enzyme variants, preferably comprising a catalytic fragment of a naturally derived enzyme, are used that are engineered with altered substrate specificity or enzymatic activity.

According to the invention it is the first time possible to provide for metabolic processing of peptides, such as natural ribosomal peptides or functionally active variants or homologues, which are displayed by a display system, including biological or in vitro display.

It turned out that the modifying processes of metabolic, enzymatic processing can be applied to replicable genetic packages displaying peptides and to peptide libraries in general. This results in intramolecular crosslinks leading to a (poly)-cyclic architecture of the peptides. Many secondary metabolites of linear peptides are derivatives from an initially larger precursor peptide. The precursor peptide in eukaryotic systems can be further subdivided in functionally different segments: At the N-terminus a signal peptide and a leader peptide are followed by the core peptide which is processed to the mature secondary metabolite and an optional recognition sequence marking the C-terminus of the precursor peptide. The proposed roles of the different segments are as follows: signal peptides direct the transport to specific subcellular compartments, signal peptides are recognition motifs for the post-translationally modifying (PTM) enzymes. The core peptide is a segment which is to be processed to become a mature secondary metabolite, and the recognition sequence is any extension at the C-terminus following the core peptide segment. Generally there are five steps involved in the production of a secondary metabolite of this group. First the messenger mRNA coding for the precursor peptide is translated using ribosomes and transport tRNAs. The precursor peptide, which can be consisting of the above mentioned segments, is then recognized by dedicated PTM enzymes which post-translationally modify the core segment resulting in molecular crosslinks leading to a (poly)-cyclic architecture. A protease cleaves off the leader peptide and thus separates the leader peptide from the core peptide segments. Finally a transport protein moves the mature secondary metabolite over a membrane. Specific mutations blocking the cleavage of the leader may be advantageous for displaying a precursor peptide according to the invention.

The present invention particularly relates to replicable genetic packages that display a peptide having at least one intramolecular cyclic bond within the amino acid side chains, specifically between two heteroatoms of amino acid side chains and methods of producing such packages, e.g. comprising
  a) providing a nucleic acid sequence encoding a peptide,
  b) ligating said nucleic acid sequence into the gene of a replicable genetic package,
  c) displaying the corresponding primary peptide sequence on the surface of said replicable genetic package to obtain a primary package, and
  d) enzymatically processing said primary package with a post-translationally modifying (PTM) enzyme to produce a mature package displaying a cyclic structure of said peptide.

The replicable genetic package according to the invention preferably is provided as a member of a library, which library members display a diversity of peptides, also called peptide library. Thus, the present invention also provides for a process of preparing a respective peptide library comprising a repertoire of replicable genetic packages displaying a variety of peptide structures.

The preferred method of producing such a library comprises
  a) providing a repertoire of nucleic acid sequences encoding peptide variants,
  b) ligating said repertoire into the genes of replicable genetic packages,
  c) displaying the corresponding primary peptide sequences on the surface of said packages to obtain a primary library, and
  d) enzymatically processing said primary library with a PTM enzyme to produce a mature library displaying cyclic structures of said peptide variants.

Therefore a repertoire of nucleic acid sequences encoding the variety of peptides can be ligated into the gene of the replicable genetic package.

To anchor the peptide to a filamentous bacteriophage surface, mostly genetic fusions to phage coat proteins are employed. Preferred are fusions to gene III, gene VIII, gene VI, gene VII and gene IX, and fragments thereof. Further-more, phage display has also been achieved on phage lambda. In that case, gene V protein, gene J protein and gene D protein are well suitable for the purpose of the invention. Besides using genetic fusions, foreign peptides or proteins have been attached to phage surfaces via association domains, including a tag displayed on phage and a tag binding ligand fused to the peptide to be displayed to achieve a noncovalent display, but also display systems including connector compounds for covalent display.

Natural ribosomal peptides are preferably used as a scaffold to prepare a repertoire of variants with different modifications at specific sites. Variants of a parent structure, such as the ribosomal peptide scaffold, are preferably grouped to form peptide libraries, which can be used for selecting members of the library with predetermined functions. In accordance therewith, a scaffold sequence is preferably randomised, e.g. through mutagenesis methods. According to preferred strategies specific positions within the peptide sequence are mutated, which provide for new bridge piers of heteroatom bridges of the heterocycle. Alternatively the mutated positions are aside from the existing bridge piers, so to generate diversity while maintaining the (poly)cyclic peptide structure.

According to a preferred embodiment a loop region or terminal region of a binding agent, such as the parent peptide sequence comprising positions within one or more loops or at a terminal site, potentially contributing to a ligand binding site, is preferably mutated or modified to produce libraries. Mutagenesis methods preferably employ random, semi-random or, in particular, by site-directed random mutagenesis, thus, resulting in a randomised sequence, in particular to delete, exchange or introduce randomly generated inserts. Alternatively preferred is the use of combinatorial approaches. Any of the known mutagenesis methods may be employed, among them cassette mutagenesis. In some cases positions and amino acids are chosen randomly, e.g. with any of the possible amino acids or a selection of preferred amino acids to randomise a sequence, or amino acid changes are made using simplistic rules. For example all residues may be mutated preferably to specific amino acids, such as alanine, referred to as amino acid or alanine scanning. Such methods may be coupled with more sophisticated engineering approaches that employ selection methods to screen higher levels of sequence diversity.

Any kind of peptide library may be subject to metabolic processing and maturation employing the PTM enzymes. Thereby the library is improved through three-dimensional, constrained structures of the peptides. This increases the chance for high affinity and/or high specificity binders.

The primary library specifically may be derived from natural ribosomal peptides used as a scaffold. However, according to another preferred embodiment any conventional peptide library may be processed by the PTM enzymes. Specifically secondary metabolites of any random peptide library can be prepared using in vivo or in vitro display technologies.

The maturation of peptide libaries through PTM enzymes according to the invention may specifically be applied to a number of display systems that link the coding function of a nucleic acid and physical, chemical and/or functional characteristics of a peptide, for example, biological display systems, including viral, e.g. bacteriophage, adenovirus or baculovirus display, fungus display, yeast display, spore display, bacteria display or ribosome display, but also in vitro display systems, including immobilised peptide display, emulsion compartmentalization and display, plasmid display, covalent display, solid phase display, microarray display and the like.

Usually peptide libraries according to the invention comprise at least $10^6$ library members, more preferred at least $10^7$, more preferred at least $10^8$, more preferred at least $10^9$, more preferred at least $10^{10}$, more preferred at least $10^{11}$, up to $10^{12}$, even higher number are feasible.

A library containing 8-mer random peptide sequence has a theoretical diversity of $2.6 \times 10^{10}$ members. To construct this library, transformants with $1.1 \times 10^{12}$ members is required in genetic diversity. To avoid experimental limitation in the construction of a complete library, either a restricted set of amino acids is used for randomisation or randomisation within a structural scaffold may be used. Loop structures typically play an important role in the molecular recognition of protein-protein or protein-peptide interactions, thus may be preferred scaffold candidate for peptide libraries are prepared according to the invention, loop structures of the heterocycles preferably be used. Preferred library designs provide for randomisation besides one or more of predetermined bridge piers of enzymatic cyclisation. For example, within the preferably used microviridin K the preferred positions for randomisation are aside from one or more of the bridge pier positions, which are $T_4$, $K_6$, $S_9$, $D_{10}$, $E_{12}$ and $E_{13}$. Other amino acids may be considered essential and thus are chosen not to be mutated, as appropriate.

According to a specific embodiment constrained peptide libraries that are chemically processed to incorporate secondary peptide structures, such as disulfide bridges, are used as primary peptide libraries to be processed by the PTM enzymes according to the invention. Thus, the enzymatic maturation of a peptide library by the PTM enzymes can add to the topographic characteristics and diversity of a peptide library.

The library or repertoire of peptides typically is combined with one or more PTM enzymes under conditions suitable for enzymatic activity. Conditions that are suitable for the enzymatic activity of PTM enzymes are well-known in the art or can be readily determined by a person of ordinary skill in the art. If desired, suitable conditions can be identified or optimized, for example, by assessing the enzymatic activity under a range of pH conditions, enzyme concentrations, temperatures and/or by varying the amount of time the library or repertoire and the enzyme are permitted to react. For example, in some embodiments, the ratio (on a mole/mole basis) of enzyme, e.g. derived from the lysate of the mutant *Planktothrix agardhii* NIVA CYA 126/8 (Philmus et al. Chembiochem (2008)3066-3073), to peptide is at least 1:100,000, preferably at least 1:10,000, more preferred at least 1:1,000, or at least 1:100, or at least 1:10, up to 1:1 (enzyme:peptide, mol/mol). The preferred range is about 0.01% to about 5% (enzyme to peptide, w/w). In one embodiment, the enzyme is used at a concentration of at least 0.01, preferably at least 0.1 or at least 0.5 ng/ml. The mixture can be incubated at a suitable temperature for enzyme activity, e.g. in the range of 20° C. to about 40° C., or at room temperature, preferably for a period of 30 min to 24 h, specifically preferred 1 h.

For example, a single enzyme, any desired combination of different enzymes, or any biological preparation, biological extract, or biological homogenate that contains enzymatic activity can be used. It is not necessary that the identity of the enzyme that is used be known. Suitable examples of enzymes that can be used alone or in any desired combination include carboxylate-amine ligase, cyclase, dehydrogenase, cyclodehydratase, lanthionine bond forming enzymes, decarboxylase, epimerase, hydroxylase, peptidase, dehydratase, transferase, esterase, oxygenase and isomerase. Preferred PTM enzymase are available from organisms or as purified enzyme preparations. In a preferred embodiment a cell lysate or enzymes derived from a cell lysate is used, such as the lysate of a mutant *Planktothrix agardhii* CYA 126/8 mvdE strain that is unable to produce microviridin by deletion of the mvdE gene (such as the strain *Planktothrix agardhii* NIVA CYA 126/8 deposited with the DSMZ Jul. 28, 2010, DSM23872), or any other appropriate strain providing the PTM enzymes may be used.

Preferred examples as used according to the invention are MvdB (accession number: ACC54548.1), MvdC (accession number: ACC54549.1) and MvdD (accession number: ACC54550.1) or their homologues like MdnB (accession number CAQ16122.1) and MdnC (accession number CAQ16123.1).

Suitable biological extracts, homogenates and preparations that contain enzymatic activity include extracts with acqueous organic solvents, lysates and the like.

According to a specific example of the invention the mvdE gene was cloned, coding for the precursor peptide of the cyanobacterial elastase inhibitor Microviridin into the bacteriophage M13 gene pIII. This mutant phage was then propagated in its host *Escherichia coli* and the M13 mutant genome was sequenced and proofed the existence of the mvdE fused to gene pIII. Subsequent immunochemical analysis showed that the mutant protein pIII showed different migration speed in a polyacrylamide gele electrophoresis indicating a physical extension compared to the wild type pIII. Both experiments proofed that the precursor peptide MvdE of Microviridin is displayed on the surface of phage M13. Microviridin is a bioactive secondary metabolite, which is produced by different cyanobacteria like *Planktothrix* spp. It is a tricyclic peptide (14mer) which is acetylated at the N-terminus and shows the amino acid sequence Acetate-YGNTMKYPSDWEEY (SEQ ID No. 1) (precursor peptide MvdE accession number EU438895.1)

Its biosynthesis is ribosomally derived including post-translational modification by PTM enzymes. The responsible gene cluster for the biosynthesis of Microviridin was identified by Philmus et al. (2008, ref. above). The mutant *Planktothrix agardhii* CYA 126/8 delta mvdE strain provided by Philmus et al. (ref. above) is unable to produce Microviridin by the deletion of the mvdE gene. Cell lysate was produced from the Microviridin deficient strain and incubated with the M13 mutant phage particles. Subsequent immunochemical analysis of the lysate treated mutant phage particles showed a different migration speed for the lysate treated pIII protein indicating a truncation of the displayed MvdE precursor peptide. This is in congruency with the steps of maturation of ribosomally derived secondary metabolites, as the leader segment is liberated from the core peptide. Therefore proof of successful maturation of the MvdE precursor peptide displayed on the nucleocapsid of a phage was obtained. Physical proof for the existence of the acetylated, tricyclic Microviridin processed from the MvdE precursor peptide displayed on the phage surface was obtained by applying methods of mass spectrometry. Polyacrylamide gel electrophoresis was used to separate and identify the lysate treated and truncated pIII-MvdE protein. After isolation of the corresponding band from the gel the protein was extracted and digested with chymotrypsin to obtain peptide fragments which can be analysed by mass spectrometry. After analysis of the masses obtained from the isolated protein a mass was detected, which was identical to the mass of the acetylated, tricyclic Microviridin. These experiments provide particular evidence for the possibility to process ribosomally derived post-translationally modified secondary metabolites on the surface of a phage.

Upon metabolic processing the library members with the appropriate peptide structures may be analysed. It may be preferred to amplify or increase the copy number of the nucleic acids that encode the selected peptides to obtain sufficient quantities of nucleic acids or peptides for additional rounds of selection or for preparing additional repertoires, e.g. for further enzymatic processing to further specific randomisation, e.g. for refining the specificity or affinity maturation purposes. For example, phage amplification, cell growth or PCR techniques may be employed. In a preferred embodiment, the display system is bacteriophage display and the amplification is through expression in *E. coli*.

A ligand binding peptide can be selected from a peptide library according to the invention using a desired binding or biological activity selection method, which allows peptides that have the desired activity to be distinguished from and selected over peptides that do not have the desired activity. Generally, one or more selection rounds are required to separate the replicable genetic package of interest from the large excess of non-binding packages. Suitable assays for peptide activity can be used to select the library members for further characterization. For example, a common ligand binding function can be assessed using a suitable binding assay, e.g. ELISA, panning. For example, peptides that bind a target ligand can be selected and recovered by panning. Panning may be accomplished by techniques well-known in the art.

Preferably screening a phage-displayed peptide library is accomplished through an affinity-selection process referred to as biopanning. Biopanning typically comprises incubating the peptide library with the target, washing away unbound phage, eluting the remaining bound phage, and amplifying the eluted phage for subsequent screening rounds. After multiple rounds of biopanning, the target-binding phage may be enriched and individual phage are isolated and sequenced to reveal any enriched binding motif.

When a phage display system is used, binding is preferably tested in a phage ELISA. Phage ELISA may be performed according to any suitable procedure. In one example, populations of phage produced at each round of selection can be screened for binding by ELISA to the selected ligand to identify phage that display ligand binding peptides. According to a commonly used procedure soluble peptides may be tested for binding to the ligand, for example by ELISA using reagents, for example, against a C- or N-terminal tag. The diversity of the selected phage may also be assessed by gel electrophoresis of PCR products or by sequencing of the vector DNA.

Depending on the target application specific peptides can also be selected based on catalytic or enzyme inhibitory activity, which can be measured using an enzyme activity assay. Further biological tests for screening suitable peptides are based on the desired antibiotic, antifungal, or otherwise bioactive, such as inhibitor or cofactoractivity, e.g. enzyme inhibitor or enhancer activity employing the suitable cell based assays.

Suitable ligand targets are preferably selected from structures or epitopes of microbes, such as bacterial, fungal, parasitic or viral, but also of human or animal cells, including proteins, specifically enzymes, co-factors for enzymes, receptors, growth factors, DNA binding proteins, nucleic acids, lipids and carbohydrates.

Binding peptides or the DNA encoding the peptides can be isolated from the replicable genetic package and characterised. Depending on the application form, the lead peptide may then be synthesized or combined with standard molecular biological techniques to make constructs encoding peptide fusions. Suitable methods of preparing the peptides or peptide fusion constructs e.g. employ recombinant expression techniques, such as expression by recombinant bacterial or yeast cells.

The peptides identified and provided according to the invention may serve as leads for development into therapeutics or diagnostic reagent, or may be manipulated to target a unique molecular entity for specific and discriminatory drug delivery. Particularly preferred applications are in the field of mimotopes of biological targets, e.g. for use as an inhibitor, such as antibacterial, antifungal, antiparasitic, antiviral, enzyme inhibitors and antibiotics, or for developing a vaccine. Further applications are feasible for industrial, analytical or environmental applications, which employ a ligand binding moiety.

A pharmaceutical composition comprising the peptide obtained according to the invention typically further comprises at least one pharmaceutically acceptable excipient well known to the skilled person. The pharmaceutical composition may further comprise at least one other biologically active agent. Suitable agents are also well known to the skilled artisan. A preferred peptide composition as obtained according to the invention may comprise stabilizing molecules, such as albumin or polyethylene glycol, or salts. Preferably, the additives used are those that retain the desired biological activity of the peptide and do not impart any undesired toxicological effects.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1

Phage Display of Microviridin

Cloning of the Chloramphenicol Acetyltransferase (CAT) Gene into the Genome of Phage M13

Genomic DNA of phage M13 was purchased from New England Biolabs, GmbH. 1 µg of DNA was incubated at 37° C. for 1 h with restriction endonuclease HindIII (Fermentas GmbH). The digested DNA was incubated at 37° C. for 20 min with Klenow fragment (Fermentas GmbH) following the recommendations of the producer. After incubation the sample was purified by using the PCR Purification Kit from Qiagen GmbH. The purified DNA was quantified using a ND-1000 spectrophotometer from NanoDrop Technologies, Inc.

Plasmid DNA pACYC184 (New England Biolabs GmbH) was used as template DNA for amplification of the CAT gene by polymerase chain reaction (PCR) using specific oligonucleotides CAT+ and CAT− purchased from MWG Eurofins GmbH and DNA Polymerase (Finnzymes Oy) following the recommendations from the producer. After termination of the PCR the sample was loaded and separated on an agarose gel (0.8%) stained with ethidiumbromide (Sigma-Aldrich GmbH). After termination the amplicon band was visualized by UV light, isolated and purified from the gel with the Gel Extraction Kit (Qiagen GmbH). The purified DNA was quantified using a ND-1000 spectrophotometer from NanoDrop Technologies, Inc.

An equimolar amount of amplified CAT DNA and phage M13 DNA was ligated using T4 DNA Ligase (Fermentas GmbH). An aliquot of the sample was used for electroporation of Escherichia coli K12 Strain 2738 (New England Biolabs) using the GenePulser (Biorad GmbH) with the standard electroporation program for Escherichia coli preinstalled on the device. The complete sample was plated out on LB-agar plates supplemented with 12.5 µg/ml of chloramphenicol (Sigma-Aldrich GmbH) and incubated at 37° C. over night. After incubation one single colony was used for inoculation of 50 ml liquid LB supplemented with 12.5 µg/ml chloramphenicol and incubated under vigorous shaking at 37° C. over night. After incubation the suspension was centrifuged in a Sorvall RCSB centrifuge Dupont, Inc. DNA from the pellet was isolated using the GeneJet Plasmid Miniprep Kit (Fermentas GmbH). The successful integration of the CAT gene into the genome of phage M13 was confirmed by DNA sequencing using a specific oligonucleotide M13Cm+ and the big dye terminator technology applied by MWG Eurofins GmbH.

Subsequently the phage was called M13KECm. DNA was double digested by the restriction endonucleases Eco52I and Acc65I (both Fermentas GmbH). After termination the sample was purified using the PCR Purification Kit (Qiagen GmbH) and DNA was quantified by spectrophotometry.

Oligonucleotides mvdE+ and mvdE− were used for amplification of the mvdE gene with DNA Polymerase (Finnzymes Oy) and template DNA from cyanobacterium Planktothrix agardhii CYA126/8 (Planktothrix agardhii NIVA CYA 126/8, DSMZ deposition date: Jul. 28, 2010, DSM23872) by PCR following the recommendations of the producer. The oligonucleotide mvdE+ carried a 6 bp extension at the 5'end generating an in frame restriction recognition sequence for Acc65I and the oligonucleotide mvdE− carried a 6 bp extension at the 5'end generating an in frame restriction recognition sequence for Eco52I. Thus the amplicon resulting from the PCR with the oligonucleotides mvdE+ and mvdE− carried both introduced restriction recognition sequences for Eco52I and Acc65I. After termination of the PCR the sample was loaded and separated on an agarose gel (3%) stained with ethidiumbromide. After termination the amplicon band was visualized by UV light isolated and purified from the gel with the Gel Extraction Kit (Qiagen GmbH). The purified DNA was quantified using a ND-1000 spectrophotometer from NanoDrop Technologies, Inc. 1 µg of the PCR product was used for double digestion with restriction endonucleases Acc65I and Eco52I (Fermentas GmbH). After incubation the sample was purified using the PCR Purification Kit (Qiagen GmbH). The purified DNA was quantified using a ND-1000 spectrophotometer (NanoDrop Technologies, Inc.).

An equimolar amount of the double digested mvdE DNA and phage M13KECm DNA was ligated using T4 DNA ligase (Fermentas GmbH). An aliquot of the sample was used for electroporation of Escherichia coli K12 strain 2738 (New England Biolabs GmbH) using the GenePulser from Biorad GmbH with the standard electroporation program for E. coli preinstalled on the device. The complete sample was plated out on LB-agar plates supplemented with 12.5 µg/ml of chloramphenicol (Sigma-Aldrich GmbH) and incubated at 37° C. over night. After incubation one single colony was used for inoculation of 50 ml liquid LB supplemented with 12.5 µg/ml chloramphenicol and incubated under vigorous shaking at 37° C. over night. After incubation the suspension was centrifuged in a Sorvall RCSB centrifuge Dupont, Inc. 10 min at 4° C. 10.000 rpm. DNA from the pellet was isolated using the GeneJet Plasmid Miniprep Kit, Fermentas GmbH.

The successful in frame integration of the mvdE gene into the pIII gene of phage M13KECm was confirmed by DNA sequencing using a specific oligonucleotide M13KE+ and the big dye terminator technology applied by MWG Eurofins GmbH.

Figures 1, 1A:
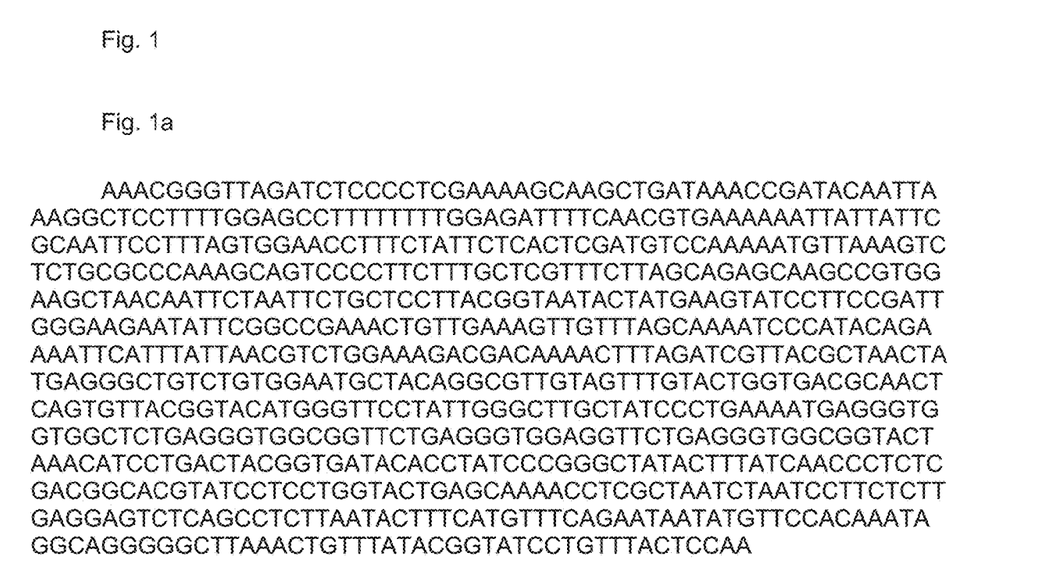
Figure 1B:
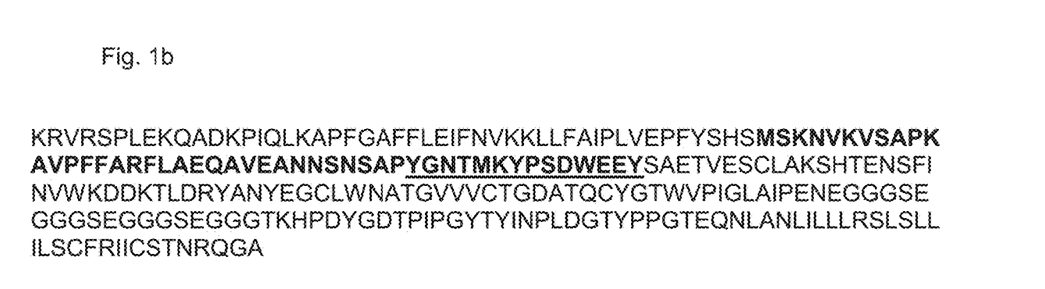

Sequences are provided in FIG. 1: Sequence of the pIII gene fused to mvdE, (FIG. 1a); translated amino acid sequence of phage protein pIII (FIG. 1b): bold letters refer to the MvdE precursor peptide, underlined letters refer to the core peptide.

Phage M13KECmMvdE Bulk Amplification

The phage was subsequently called M13KECmMvdE. 100 ng DNA was used for electroporation of *Escherichia coli* K12 strain 2738 New England Biolabs GmbH using the GenePulser (Biorad GmbH) with the standard electroporation program for *Escherichia coli* preinstalled on the device. The complete sample was plated out on LB-agar plates supplemented with 12.5 µg/ml of chloramphenicol and incubated at 37° C. over night. After incubation one single colony was used for inoculation of 3 ml liquid LB supplemented with 12.5 µg/ml chloramphenicol and incubated under vigorous shaking at 37° C. over night. After incubation 300 µl of the suspension was used to inoculate 300 ml liquid LB supplemented with 12.5 µg/ml chloramphenicol and incubated under vigorous shaking at 37° C. for 4.5 h. After incubation the suspension was centrifuged for 10 min at 4° C. in a Sorvall RCSB centrifuge Dupont, Inc. and the supernatant was transferred to a fresh bucket and recentrifuged under the same conditions. The supernatant (280 ml) was then transferred to a fresh bucket and 45 ml PEG-NaCl buffer (20% (w/v) polyethylene glycol-8000, 2.5M NaCl (Sigma-Aldrich GmbH) were added, vigorously mixed and incubated at 4° C. over night. The sample was centrifuged for 15 min at 10.000 rpm at 4° C. in a Sorvall RCSB centrifuge (Dupont, Inc.). After centrifugation the supernatant was completely removed and the white pellet was resuspended in 2 ml of TBS buffer (50 mM TRis-HCl pH7.5, 150 mM NaCl, Sigma-Aldrich GmbH) and stored at 4° C.

Analogously phage M13KECm was produced in bulk quantities and stored at 4° C.

Polyacrylamid Gelelectrophoresis (PAGE) of the Phage Particles

All PAGE analyses were performed with a gel strength of 6% using a MiniProtean Cell (Biorad GmbH). A total of 10 µl of the phage samples M13KECm (negative control) and M13KECmMvdE were loaded on the gel and separated following the guidelines of the producer. After termination the gel was blotted on a PVDF membrane (Biorad GmbH) by semi-dry blotting procedure recommended by the producer. The membrane was used for immunochemical analysis using a primary antibody against the pIII protein of phage M13 obtained from New England Biolabs GmbH. After development of the membrane a clear size difference between the pIII band of phage M13KECm and pIII of phage M13KECmMvdE was visible indicating a size extension of pIII in the phage of M13KECmMvdE.

Lysate Treatment of Phage M13KECmMvdE 150 ml of the mutant strain of the cyanobacterium *Planktothrix agardhii* CYA 126/8 DelMvdE (Philmus et al (2008) Chembiochem. 9(18):3066-73) was centrifuged and washed three times with TE buffer (10 mM EDTA pH8 1 mM Tris-HCl pH8 Sigma-Aldrich GmbH). After final centrifugation the cell pellet was resuspended in 1 ml of 20 mM Tris-HCl pH8.3 and freshly added beta-mercaptoethanol to a final concentration of 10 mM both obtained from Sigma-Aldrich GmbH. All subsequent steps were performed on ice. The suspension was transferred to a cell disruption vessel (Parr Instrument GmbH) and pressure of 110 bar was applied before passaging the suspension through the valve. Three of those cycles were performed and after completion the suspension was centrifuged for 10 min at 10.000 rpm, 4° C. in a Sorvall RCSB centrifuge Dupont, Inc. The supernatant was transferred to a fresh tube and kept on ice until further use.

100 µl of phage suspension M13KECmMvdE were mixed with 500 µl of the above described lysate and incubated at 22° C. for 1 h. After termination the suspension was treated with 1/6 volume of PEG/NaCl buffer and incubated over night at 4° C. The sample was centrifuged for 15 min at 10.000 rpm at 4° C. in a Sorvall RCSB centrifuge Dupont, Inc. After centrifugation the supernatant was completely removed and the greenish pellet was resuspended in 1 ml of TBS buffer (50 mM TRis-HCl pH7.5, 150 mM NaCl) and stored at 4° C. A second wash step was applied following the above described procedure. Finally the pellet was resuspended in 40 µl TBS. A total of 30 µl of the phage samples M13KECmMvdE without lysate treatment (negative control) and M13KECmMvdE after lysate treatment were loaded on the gel and separated following the guidelines of the producer. After termination the gel was blotted on a PVDF membrane (Biorad GmbH) by semi-dry blotting procedure recommended by the producer. The membrane was used for immunochemical analysis using a primary antibody against the pIII protein of phage M13 obtained from New England Biolabs GmbH. After development of the membrane a clear size difference between the pIII band of phage M13KECmMvdE without lysate treatment and pIII of phage M13KECmMvdE with lysate treatment was visible indicating a size truncation of pIII in the phage of M13KECmMvdE. This size difference was interpreted that after successful post translational modification of the precursor peptide displayed on the phage nucleocapsid it should be 35 amino acids shorter.

The SDS PAGE was repeated as described obove and the gel was used for commassie staining (Biorad GmbH). The protein band of pIII of the phage M13KECmMvdE lysate treated was isolated and used for mass spectrometry. Mass spectrometry was performed by Proteom Factory GmbH. The protein band was washed by adding and removing 100 mM Tris-HCl (Sigma Aldrich) for 20 minutes followed by 100 mM Tris-HCl, 10 mM CaCl2 (Sigma Aldrich), 80% Acetonitrile (VWR International) (v/v), pH 8.0 for 20 minutes. After repeating the washing steps twice the supernatant was removed and 200 ng chymotrypsin was added in 20 µl 100 mM Tris-HCl, 10 mM CaCl2, 5% ACN (v/v), pH 8.0 to the protein band for digestion over night at 25° C. The solution was acidified with 1 Vol 2% formic acid and incubated for 30 minutes. Microviridin K pure substance (Philmus et al 2008, ref. above) was isolated from the strain *Planktothrix agardhii* CYA 126/8 by HPLC (Hewlett&Packard Inc.) using a gradient described in Kosol et al (2009 Eur. J. Phycol. 44:49-62).

Approximately 10 ng of the pure peptide was incubated with 200 ng chymotrypsin in 20 µl 100 mM Tris-HCl, 10 mM CaCl2, 5% Acetonitrile (v/v), pH 8.0 over night at 25° C. After incubation the solution was acidified with 1 Vol 2% formic acid and incubated for 30 minutes. 20 µl of both samples were applied to high resolution nanoLC-ESI-MS (Thermo FT-ICR MS) analyses using a 50 min nanoLC gradient (Agilent 1100 nanoLC system) with solvent A (0.1% formic acid/5% acetonitrile/94.9% ddH2O) and solvent B (0.1% formic acid/99.9% acetonitrile) starting from 5% B to 40% B. The mass accuracy was better 5 ppm for MS and better 0.5 Da for MSMS data. The MS data were analyzed by Mascot server using a custom database with the amino acid sequence of the analyzed protein.

Theoretical mass calculation: monoisotopic mass of the microviridin K is 1771.70038 Da (Philmus et al 2008) which results in 885.85019 Da for a double charged mass m/z.

Figure 2:
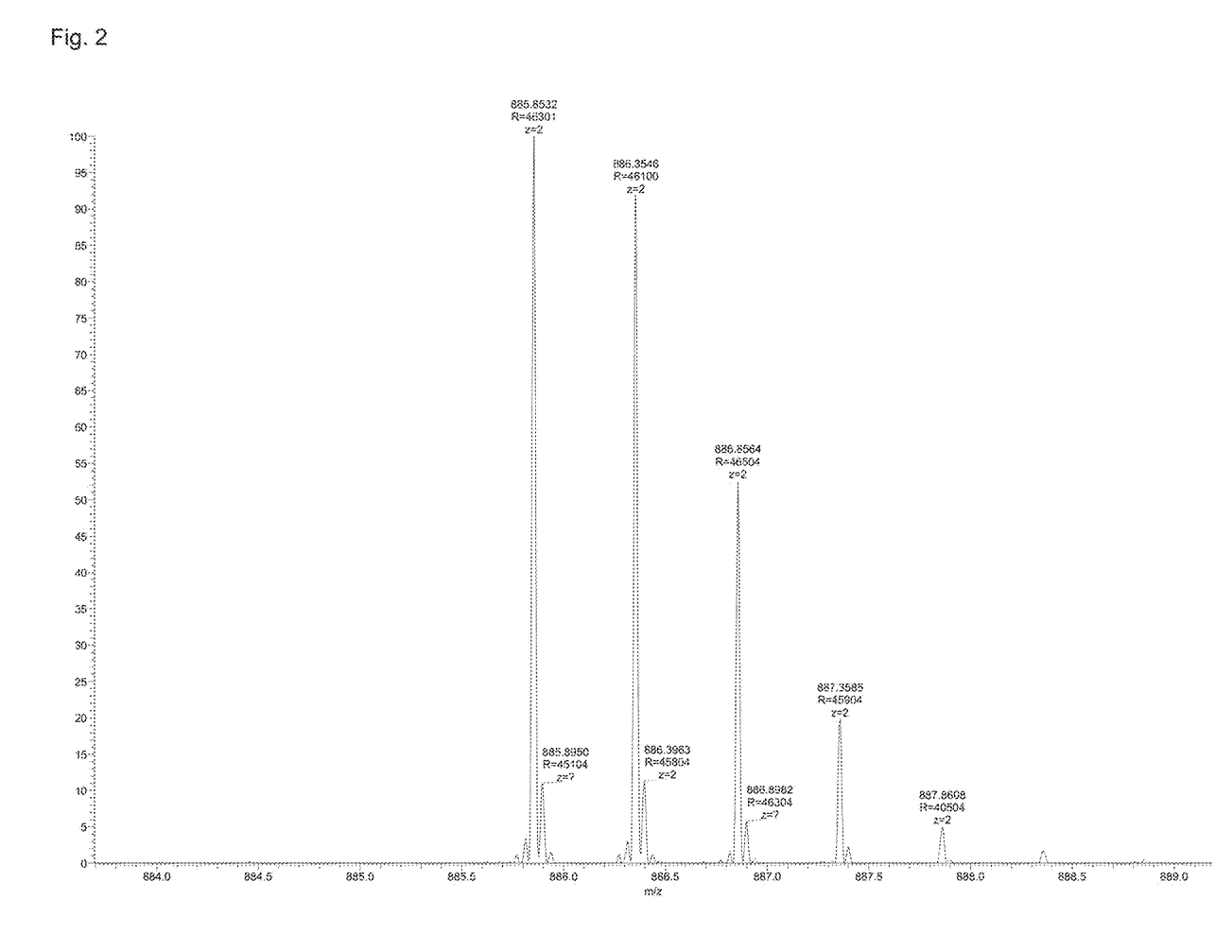
FIG. 2: High resolution mass spectrum (FTMS) of the chymotrypsin treated reference peptide Microviridin K. The shown mass of 885.8532 Da matches the theoretical mass (885.85019 Da) of Microviridin K.
Figure 3:
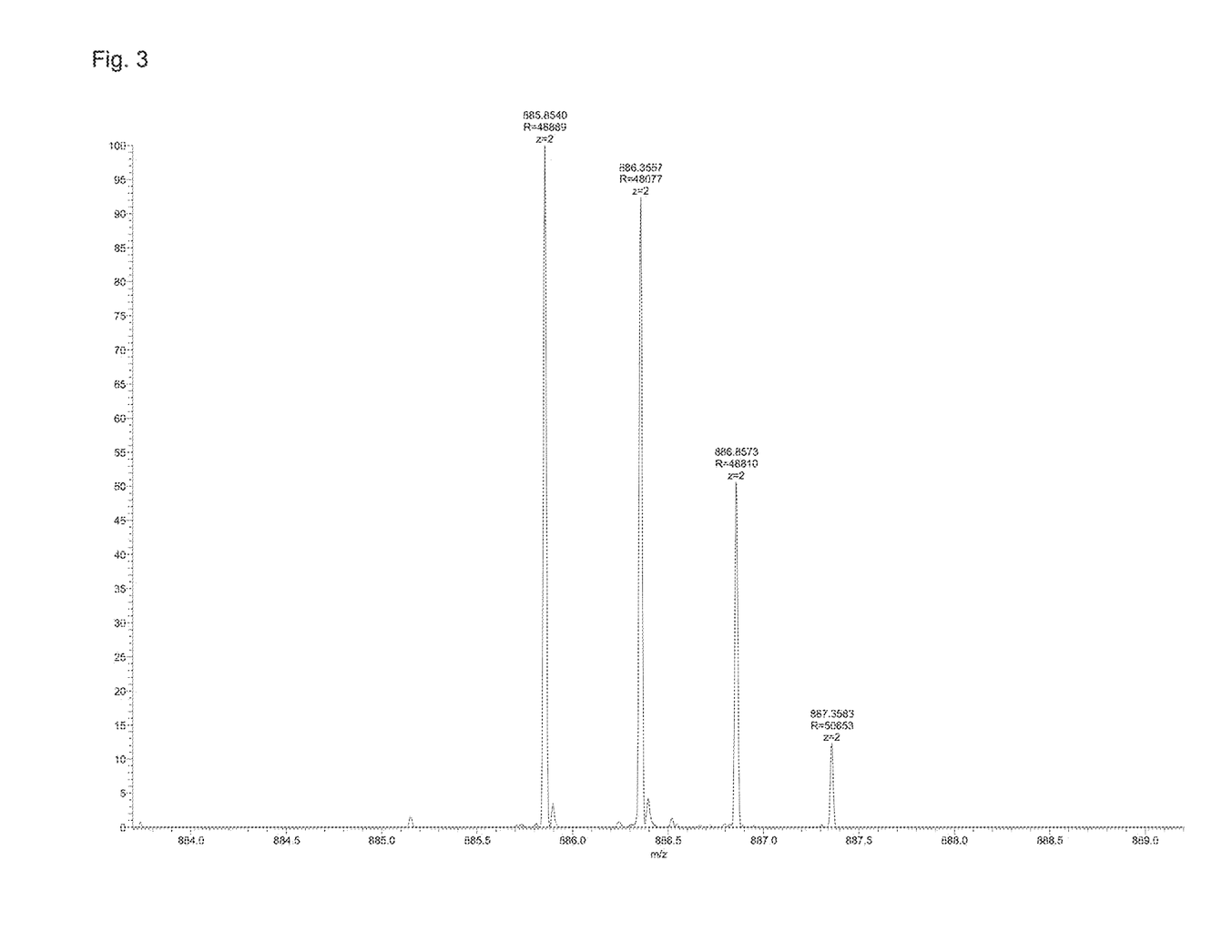
FIG. 3. High resolution mass spectrum (FTMS) of the chymotryptic digested sample band separated by SDS-PAGE. The sample referes to the PTM enzyme treated M13KECmMvdE phage. The detected double charged mass m/z 885.8540 Da fits well to the theoretical mass of peptide Microviridin K and the measured mass of reference peptide Microviridin K (FIG. 1). The mass accuracy was 5 ppm.

Results are provided in FIGS. 2 (reference) and 3 (M13KECmMvdE).

Interpretation:

The acetylated, tricyclic peptide Microviridin K was isolated by HPLC and approximately 10 ng of the pure peptide was treated with chymotrypsin prior to measurement with FTMS. A mass of 885.8532 Da could be detected which fits well with the theoretically calculated mass of 885.85019 Da for Microviridin K. Therefore the chymotrypsin treatment of the pure Microviridin did not result in cleavage of the peptide, which is in agreement to the cyclic nature of Microviridin K.

The sample used in the second FTMS measurement represents the isolated pIII protein of phage M13KECmMvdE. The phage M13KECmMvdE displays a pIII protein which has been N-terminally fused to the precursor protein of MvdE and the phage was treated with cell lysate of *Planktothrix agardhii* NIVA CYA 126/8 DelMvdE. The so treated phages M13KECmMvdE were used for SDS PAGE separation and the protein band representing the modified pIII-MvdE protein was isolated and extracted from the gel. After successful processing of the displayed pIII-MvdE with the PTM enzymes from the lysate a generated tricyclic Microviridin K is supposed to be attached N-terminally to the pIII protein. The C-terminal amino acid of Microviridin K is a tyrosine. As chymotrypsin is a proteolytic enzyme which preferentially cleaves amide bonds where the carboxyl side of the amide bond is a tyrosine it was used to cleave exactly after the Microviridin K and liberate it from phage protein pIII. Indeed the mass spectrum depicted in FIG. 3 shows a mass which is identical within the mass accuracy of 5 ppm to the reference mass as shown in FIG. 2. This is evidence that the displayed precursor peptide MvdE was completely post translationally modified by the PTM enzymes while being attached and displayed onto the phage M13KECmMvdE using PTM enzymes contained in the lysate of *Planktothrix agardhii* NIVA CYA 126/8 DelMvdE.

The data described here are evident that a member of the post translationally modified peptides (Microviridin) can be generated while physically linked to a nucleocapsid protein of a virus.

Example 2

Creating a Peptide Library

Microviridin K is tricyclic peptide with the amino acid sequence $Y_1G_2N_3T_4M_5K_6Y_7P_8S_9D_{10}W_{11}E_{12}E_{13}Y_{14}$ (see SEQ ID No. 1) where amino acid residues involved in the intramolecular cross linking are $T_4$, $K_6$, $S_9$, $D_{10}$, $E_{12}$ and $E_{13}$. Therefore positions 1, 2, 3, 5, 7, 8, 11, 14 are considered variable and preferably used for randomisation without interference with the numbers of bridges and bridging pattern. Randomisation of the amino acid residues at position 1, 2, 3, 5, 7, 8, 11, 14 is done by elaboration of an oligonucleotide mixture obtained from solid phase synthesis (MWG Eurofins GmbH).

The oligonucleotide sequence is as follows: $(NNK)_n$.ACT.NNK.AAG.NNK.NNK.TCC.GAT.NNK. GAA.GAA.$(NNK)_n$ (SEQ ID No. 4). Diversity is typically introduced into a phage-displayed peptide library by randomising library oligonucleotide DNA through the use of a reduced genetic code. For example, the degenerate codon NNK (where N represents a 25% mix each of adenine, thymine, guanine, and cytosine nucleotides; and K represents a 50% mix each of thymine and guanine nucleotides) is used in the library DNA construction. The triplets, e.g. encloding $T_4$ may as well be ACC, ACG, ACA. The same strategy may be employed for $K_6$ with the additional possibilty of triplett AAA and for the other positions 9, 10, 12 and 13. Also extensions of different triplet numbers at the 5'end as well as 3'end is elaborated by addition of $(NNK)n$ triplets (N=GATC and K=GT, n is an integer between 0 and 100. Integration of the oligonucleotides into the gene coding for pIII is done following established protocols (eg Sambrock and Russel 2001, Molecular cloning, $3^{rd}$ edition CSHL Press). Post-translational modification of the precursor MvdE peptide displayed on the phages is done also with purified enzymes among others MvdB (accession number: ACC54548.1), MvdC (accession number: ACC54549.1) and MvdD (accession number: ACC54550.1) or their homologues like MdnB (accession number CAQ16122.1) and MdnC (accession number CAQ16123.1).

Post-translationally modified peptides which are also described in Oman & van der Donk (2010) (Nat Chem Biol. 2010 January; 6(1):9-18) can be subdivided in two principally different classes: One class is constituted by members like microviridins, lacticins, thiostreptons, conopeptides amongst others which have the common feature that the C-terminal amino acid of the precursor peptide is also the C-terminal amino acid of the fully processed core peptide. Members of the second class like the patellamides, amanitins amongst others show the common feature that they are proteolytically excised from the precursor peptide. For the first mentioned class it is possible to link their precursor peptides with a nucleocapsid protein of a virus and process them being displayed with either lysates from the producer organism or with dedicated purified PTM enzymes and keep them linked to the virus as their biosynthesis does not involve steps where the core peptide is separated from the C-terminal amino acid of the precursor peptide. Therefore the physical linkage between genetic information and the structure displayed on the surface of a virus is maintained for all representatives of class one PTM peptides during all steps of their biosynthesis.

The invention claimed is:

1. A replicable genetic package, which is a phage particle, displaying a peptide comprising a core peptide portion having a plurality of amino acid side chains and at least one intramolecular cyclic bond between two atoms of the amino acid side chains, wherein the cyclic bond is between C—S, and wherein said core peptide is formed by reaction of a primary peptide with a lanthionine bond forming enzyme.

2. The replicable genetic package according to claim 1, wherein the cyclic bond between C—S is a lanthionine or methyllanthionine bond.

3. The replicable genetic package according to claim 1, wherein the lanthionine bond forming enzyme is selected from (i) a combination of LanB and Lan C, and (ii) LanM.

4. The replicable genetic package according to claim 1, which is selected from the group consisting of M13, T4, 17, fd and lambda phages.

5. The replicable genetic package according to claim 1, wherein said primary peptide is a precursor peptide comprising a leader and a core-forming peptide.

6. The replicable genetic package according to claim 1, wherein said core peptide is derived from a natural ribosomal peptide.

7. The replicable genetic package according to claim 1, wherein said core peptide comprises a polycyclic structure.

8. A collection of replicable genetic packages according to claim 1, wherein each member of said collection displays one member of a diverse collection of peptides.

9. The collection of claim 8, wherein said diverse collection of peptides is obtainable by randomization of one of more amino acid residues of a precursor peptide.

10. The collection of claim 9, wherein said diverse collection of peptides is obtainable by (a) providing a repertoire of nucleic acid sequences encoding said diverse collection and b) ligating said repertoire into a gene of said replicable genetic package.

* * * * *

SEQUENCE LISTING

<160> NUMBER OF SEQ ID NOS: 4

<210> SEQ ID NO 1

```
<211> LENGTH: 14
<212> TYPE: PRT
<213> ORGANISM: Planktothrix

<400> SEQUENCE: 1

Tyr Gly Asn Thr Met Lys Tyr Pro Ser Asp Trp Glu Glu Tyr
 1               5                  10

<210> SEQ ID NO 2
<211> LENGTH: 764
<212> TYPE: DNA
<213> ORGANISM: artificial
<220> FEATURE:
<223> OTHER INFORMATION: modified phage

<400> SEQUENCE: 2
aaacgggtta gatctcccct cgaaaagcaa gctgataaac cgatacaatt aaaggctcct      60
tttggagcct ttttttttgga gattttcaac gtgaaaaaat tattattcgc aattcctttta    120 gtggaacctt tctattctca ctcgatgtcc aaaaatgtta agtctctgc gcccaaagca      180 gtccccttct ttgctcgttt cttagcagag caagccgtgg aagctaacaa ttctaattct     240 gctcctttacg gtaatactat gaagtatcct tccgattggg aagaatattc ggccgaaact    300
gttgaaagtt gtttagcaaa atcccataca gaaaattcat ttattaacgt ctggaaagac    360
gacaaaactt tagatcgtta cgctaactat gagggctgtc tgtggaatgc acaggcgtt    420 gtagtttgta ctggtgacgc aactcagtgt tacggtacat gggttcctat tgggcttgct    480
atccctgaaa atgagggtgg tggctctgag ggtggcggtt ctgagggtgg aggttctgag   540
ggtggcggta ctaaacatcc tgactacggt gatacaccta tcccgggcta ctttatca     600 accctctcga cggcacgtat cctcctggta ctgagcaaaa cctcgctaat ctaatccttc    660
tcttgaggag tctcagcctc ttaatacttt catgtttcag aataatatgt tccacaaata    720 ggcaggggc ttaaactgtt tatacggtat cctgtttact ccaa                    764

<210> SEQ ID NO 3
<211> LENGTH: 244
<212> TYPE: PRT
<213> ORGANISM: artificial
<220> FEATURE:
<223> OTHER INFORMATION: modified phage

<400> SEQUENCE: 3

Lys Arg Val Arg Ser Pro Leu Glu Lys Gln Ala Asp Lys Pro Ile Gln
 1               5                  10                  15

Leu Lys Ala Pro Phe Gly Ala Phe Phe Leu Glu Ile Phe Asn Val Lys
                20                  25                  30

Lys Leu Leu Phe Ala Ile Pro Leu Val Glu Pro Phe Tyr Ser His Ser
            35                  40                  45

Met Ser Lys Asn Val Lys Val Ser Ala Pro Lys Ala Val Pro Phe Phe
        50                  55                  60

Ala Arg Phe Leu Ala Glu Gln Ala Val Glu Ala Asn Asn Ser Asn Ser
 65                  70                  75                  80

Ala Pro Tyr Gly Asn Thr Met Lys Tyr Pro Ser Asp Trp Glu Glu Tyr
                85                  90                  95

Ser Ala Glu Thr Val Glu Ser Cys Leu Ala Lys Ser His Thr Glu Asn
            100                 105                 110

Ser Phe Ile Asn Val Trp Lys Asp Asp Lys Thr Leu Asp Arg Tyr Ala
        115                 120                 125
```

```
Asn Tyr Glu Gly Cys Leu Trp Asn Ala Thr Gly Val Val Cys Thr
        130                 135                 140

Gly Asp Ala Thr Gln Cys Tyr Gly Thr Trp Val Pro Ile Gly Leu Ala
145                 150                 155                 160

Ile Pro Glu Asn Glu Gly Gly Ser Glu Gly Gly Ser Glu Gly
            165                 170                 175

Gly Gly Ser Glu Gly Gly Thr Lys His Pro Asp Tyr Gly Asp Thr
        180                 185                 190

Pro Ile Pro Gly Tyr Thr Tyr Ile Asn Pro Leu Asp Gly Thr Tyr Pro
        195                 200                 205

Pro Gly Thr Glu Gln Asn Leu Ala Asn Leu Ile Leu Leu Arg Ser
        210                 215                 220

Leu Ser Leu Leu Ile Leu Ser Cys Phe Arg Ile Ile Cys Ser Thr Asn
225                 230                 235                 240

Arg Gln Gly Ala

<210> SEQ ID NO 4
<211> LENGTH: 36
<212> TYPE: DNA
<213> ORGANISM: artificial
<220> FEATURE:
<223> OTHER INFORMATION: randomised peptide
<220> FEATURE:
<221> NAME/KEY: misc_feature
<222> LOCATION: (1)..(2)
<223> OTHER INFORMATION: n is a, c, g or t
<220> FEATURE:
<221> NAME/KEY: misc_feature
<222> LOCATION: (3)..(3)
<223> OTHER INFORMATION: k is g or t
<220> FEATURE:
<221> NAME/KEY: misc_feature
<222> LOCATION: (7)..(8)
<223> OTHER INFORMATION: n is a, c, g or t
<220> FEATURE:
<221> NAME/KEY: misc_feature
<222> LOCATION: (9)..(9)
<223> OTHER INFORMATION: k is g or t
<220> FEATURE:
<221> NAME/KEY: misc_feature
<222> LOCATION: (13)..(14)
<223> OTHER INFORMATION: n is a, c, g or t
<220> FEATURE:
<221> NAME/KEY: misc_feature
<222> LOCATION: (15)..(15)
<223> OTHER INFORMATION: k is g or t
<220> FEATURE:
<221> NAME/KEY: misc_feature
<222> LOCATION: (16)..(17)
<223> OTHER INFORMATION: n is a, c, g or t
<220> FEATURE:
<221> NAME/KEY: misc_feature
<222> LOCATION: (18)..(18)
<223> OTHER INFORMATION: k is g or t
<220> FEATURE:
<221> NAME/KEY: misc_feature
<222> LOCATION: (25)..(26)
<223> OTHER INFORMATION: n is a, c, g or t
<220> FEATURE:
<221> NAME/KEY: misc_feature
<222> LOCATION: (27)..(27)
<223> OTHER INFORMATION: k is g or t
<220> FEATURE:
<221> NAME/KEY: misc_feature
<222> LOCATION: (34)..(35)
<223> OTHER INFORMATION: n is a, c, g or t
<220> FEATURE:
```

```
<221> NAME/KEY: misc_feature
<222> LOCATION: (36)..(36)
<223> OTHER INFORMATION: k is g or t

<400> SEQUENCE: 4
nnkactnnka agnnknnktc cgatnnkgaa gaannk                                    36
```